(12) United States Patent
Hlavinka et al.

(10) Patent No.: US 9,416,087 B2
(45) Date of Patent: Aug. 16, 2016

(54) METHODS FOR THE PRODUCTION OF α,β-UNSATURATED CARBOXYLIC ACIDS AND SALTS THEREOF

(71) Applicant: Chevron Phillips Chemical Company LP, The Woodlands, TX (US)

(72) Inventors: Mark L. Hlavinka, Tulsa, OK (US); Max P. McDaniel, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/509,082

(22) Filed: Oct. 8, 2014

(65) Prior Publication Data

US 2016/0102039 A1 Apr. 14, 2016

(51) Int. Cl.
| | |
|---|---|
| C07C 51/377 | (2006.01) |
| B01J 31/22 | (2006.01) |
| B01J 31/26 | (2006.01) |
| B01J 31/14 | (2006.01) |
| B01J 31/12 | (2006.01) |
| B01J 31/38 | (2006.01) |
| C07C 51/15 | (2006.01) |

(52) U.S. Cl.
CPC ............ *C07C 51/377* (2013.01); *B01J 31/128* (2013.01); *B01J 31/143* (2013.01); *B01J 31/2295* (2013.01); *B01J 31/26* (2013.01); *B01J 31/38* (2013.01); *C07C 51/15* (2013.01); *B01J 2231/46* (2013.01); *B01J 2531/847* (2013.01)

(58) Field of Classification Search
CPC ...... C07C 51/41; C07C 57/04; C07C 51/377; C07C 51/15; C07C 51/418; C07F 15/04; B01J 31/26; B01J 31/2295; B01J 31/143; B01J 31/128; B01J 31/38; B01J 2531/847; B01J 2231/46
USPC ................................................ 562/550, 551
See application file for complete search history.

(56) References Cited

U.S. PATENT DOCUMENTS

| | | | |
|---|---|---|---|
| 4,060,480 A | 11/1977 | Reed | |
| 4,452,910 A | 6/1984 | Hopkins | |
| 5,376,611 A | 12/1994 | Shveima | |
| 6,107,230 A | 8/2000 | McDaniel et al. | |
| 6,165,929 A | 12/2000 | McDaniel et al. | |
| 6,294,494 B1 | 9/2001 | McDaniel et al. | |
| 6,300,271 B1 | 10/2001 | McDaniel et al. | |
| 6,316,553 B1 | 11/2001 | McDaniel et al. | |
| 6,355,594 B1 | 3/2002 | McDaniel et al. | |
| 6,376,415 B1 | 4/2002 | McDaniel et al. | |
| 6,388,017 B1 | 5/2002 | McDaniel et al. | |
| 6,391,816 B1 | 5/2002 | McDaniel et al. | |
| 6,395,666 B1 | 5/2002 | McDaniel et al. | |
| 6,524,987 B1 | 2/2003 | Collins et al. | |
| 6,548,441 B1 | 4/2003 | McDaniel et al. | |
| 6,548,442 B1 | 4/2003 | McDaniel et al. | |
| 6,576,583 B1 | 6/2003 | McDaniel et al. | |
| 6,613,712 B1 | 9/2003 | McDaniel et al. | |
| 6,632,894 B1 | 10/2003 | McDaniel et al. | |
| 6,667,274 B1 | 12/2003 | Hawley et al. | |
| 6,750,302 B1 | 6/2004 | McDaniel et al. | |
| 7,250,510 B2 | 7/2007 | Organ et al. | |
| 7,294,599 B2 | 11/2007 | Jensen et al. | |
| 7,601,665 B2 | 10/2009 | McDaniel et al. | |
| 7,884,163 B2 | 2/2011 | McDaniel et al. | |
| 8,309,485 B2 | 11/2012 | Yang et al. | |
| 8,592,632 B2 | 11/2013 | Dahmen et al. | |
| 8,642,803 B2 | 2/2014 | Limbach et al. | |
| 8,697,909 B2 | 4/2014 | Limbach et al. | |
| 8,940,940 B2 | 1/2015 | Dehn et al. | |
| 2011/0218359 A1* | 9/2011 | Limbach ................. | C07C 51/14 562/522 |
| 2013/0172616 A1 | 7/2013 | Limbach et al. | |
| 2015/0343431 A1 | 12/2015 | Parvulescu et al. | |
| 2015/0344394 A1 | 12/2015 | Parvulescu et al. | |

FOREIGN PATENT DOCUMENTS

| | | |
|---|---|---|
| CN | 104418719 A | 3/2015 |
| CN | 104418736 A | 3/2015 |
| CN | 104418737 A | 3/2015 |
| DE | 11 2014 001 125 A5 | 11/2015 |
| EP | 2 797 869 A4 | 8/2015 |
| IN | 201207472 P4 | 12/2013 |
| IN | 201404656 P4 | 9/2015 |
| WO | WO 2011/107559 | 9/2011 |
| WO | WO 2013/098772 | 7/2013 |
| WO | WO 2013/186238 | 12/2013 |
| WO | WO 2014/003195 A1 | 1/2014 |
| WO | WO 2014/130410 A1 | 8/2014 |
| WO | WO 2014/198469 A1 | 12/2014 |

(Continued)

OTHER PUBLICATIONS

Yu "Carboxylation of olefins/alkynes with CO2 to industrially relevant acrylic acid derivatives" Journal of CO2 Utilization (2013) 60-68.*

Kirillov "Carboxylic acid derivative via catalytic carboxylation of unsaturated hydrocarbons: whether the nature of a reductant may determine the mechanism of CO2 incorporation" Dalton Transactions (2015) 44, 16212-16223.*

(Continued)

Primary Examiner — Jafar Parsa
Assistant Examiner — Amy C Bonaparte
(74) Attorney, Agent, or Firm — Merchant & Gould P.C.

(57) ABSTRACT

Processes for producing an α,β-unsaturated carboxylic acid, such as acrylic acid, or a salt thereof, using solid promoters are disclosed. The solid promoters can be certain solid oxides, mixed oxides, and clays, illustrative examples of which can include alumina, zirconia, magnesia, magnesium aluminate, sepiolite, and similar materials.

19 Claims, No Drawings

(56) References Cited

FOREIGN PATENT DOCUMENTS

| WO | WO 2015/018793 | 2/2015 |
|---|---|---|
| WO | WO 2015/132031 A1 | 9/2015 |
| WO | WO 2015/173276 | 11/2015 |
| WO | WO 2015/173277 | 11/2015 |
| WO | WO 2015/173295 | 11/2015 |
| WO | WO 2015/173296 | 11/2015 |
| WO | WO 2015/173307 | 11/2015 |
| WO | WO 2015/197699 | 12/2015 |

OTHER PUBLICATIONS

Bruckmeier et al., "Formation of Methyl Acrulate from $CO_2$ and Ethylene via Methylation of Nickelalactones"; Organometallics, 2010, vol. 29, No. 10, pp. 2199-2202.

Fischer et al., "A key step in the formation of acrylic acid from $CO_2$ and ethylene: the transformation of a nickelalactone into a nickel-acrylate complex"; Chem Commun., 2006, pp. 2510-2512.

Fischer et al., "Zur Synthese und Charakterisierung von N,N'—Tetramethylethylendiamin-nickelacyclopropionat"; Z. anorg. allg. Chem., 1989, 577, pp. 111-114.

Hoberg et al., "Nickel(O)-Induzierte C—C-Verknüpfung Zwischen Kohlendioxid und Ethylen Sowie Mono-Oder Di-Substituierten Alkenen"; Journal of Organometallic Chemistry; 1983, 251, pp. C51-C53.

Jin et al., "Effect of Sodium Cation on Metallacycle β- Hydride Elimination in $CO_2$-Ethylene Coupling to Acrylates"; Chem. Eur. J., 2014, vol. 20, pp. 1-8.

Jin et. al., "Lewis Acid Induced β- Elimination from a Nickelatactone: Efforts toward Acrylate Production from $CO_2$ and Ethylene"; Department of Chemistry, Brown University, Providence RI; Department of Chemistry, Yale University, New Haven, CT; pubs.acs.org/Organometallics; 2013, pp. A-H, 8 pgs.

Langer et al., "A new set of nickelacyclic carboxylates ("nickelalactones") containing pyridine as supporting ligand: synthesis, structures and application in C—C- and C—S linkage reactions"; Journal of Organometallic Chemistry, 2004, 689, pp. 2952-2962.

Lejkowski et al., "The First Catalytic Synthesis of an Acrylate from $CO_2$ and an Alkene—A Rational Approach"; Chem. Eur. J., 2012, 18, pp. 14017-14025.

Pápai et al., "Mechanistic Details of Nickel(0)-Assisted Oxidative Coupling of $CO_2$ with $C_2H_4$"; Chemical Research Centre of the Hungarian Academy of Sciences; Organometallics, 2004, 23, pp. 5252-5259.

Pinnavaia, T. J., "Intercalated Clay Catalysts," Science, 1983, vol. 220, No. 4595, pp. 365-371.

Thomas, J. M., "Sheet Silicate Intercalates: New Agents for Unusual Chemical Conversions," Intercalation Chemistry, Academic Press, Inc., 1982, Ch. 3, pp. 55-99.

International Search Report and Written Opinion of the International Searching Authority, PCT/US2015/054128, dated Dec. 21, 2015, 11 pages.

Gordillo, et al., "Catalytic route to acrylates from alkenes and $CO_2$," ACS Abstracts, 245th ACS National Mtg, 2013, INOR-1109, 4-7 to 11.

Huguet, et al., "Nickel-Catalyzed Direct Carboxylation of Olefins with $CO_2$: One-Pot Synthesis of α,β-Unsaturated Carboxylic Acid Salts," Chem. Eur. J. 2014, 20, pp. 16858-16862.

Limbach, et al., "$CO_2$ as C1 building block for the synthesis of acrylates and beyond," ACS Abstracts, 247th ACS National Mtg, CATL-116, 2014, 3-16 to 20.

Limbach, et al., "Investigation of fundamental steps in the formation of acrylates from $CO_2$ and ethylene," ACS Abstracts, 243rd ACS National Mtg, 2012, INOR-1216, 3-29.

Plessow, et al., "Acrylate Formation from $CO_2$ and Ethylene Mediated by Nickel Complexes: A Theoretical Study," Organometallics, 2014, vol. 33, 3657-3668.

Plessow, et al., "Mechanistic Details of the Nickel-Mediated Formation of Acrylates from $CO_2$, Ethylene and Methyl Iodide," Organometallics, 2013, vol. 32, pp. 3327-3338.

Stieber, et al., "Acrylate formation from $CO_2$ and ethylene: catalysis with palladium and mechanistic insight," Chem. Commun., 2015, vol. 51, pp. 10907-10909.

* cited by examiner

US 9,416,087 B2

METHODS FOR THE PRODUCTION OF α,β-UNSATURATED CARBOXYLIC ACIDS AND SALTS THEREOF

BACKGROUND OF THE INVENTION

The majority of industrially synthesized chemical compounds are prepared from a limited set of precursors, whose sources are ultimately fossil fuels. It would be beneficial to use a renewable resource, such as carbon dioxide, which is a non-toxic, abundant, and economical $C_1$ synthetic unit. The coupling of carbon dioxide and olefins holds tremendous promise as one could envision the direct preparation of acrylates and carboxylic acids through this method. Currently, acrylic acid is produced via a two-stage oxidation of propylene. The production of acrylic acid directly from carbon dioxide and ethylene would represent a significant improvement due to the greater availability of ethylene and carbon dioxide versus propylene, the use of a renewable material ($CO_2$) in the synthesis, and the replacement of the two-step oxygenation process currently being practiced. Accordingly, it is to these ends that the present invention is directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Processes for producing an α,β-unsaturated carboxylic acid, or a salt thereof, are disclosed herein. These processes represent an improvement over homogeneous processes that result in poor yields and have challenging separation/isolation procedures, due in part to the reaction being conducted in an organic solvent, making isolation of the desired α,β-unsaturated carboxylic acid (e.g., acrylic acid) difficult. In contrast, the processes disclosed herein utilize a solid promoter (or solid activator), providing a heterogeneous system that has a distinct advantage in ease of separation of the desired product from the catalytic promoter. Moreover, the solid promoters can result in surprisingly high yields of the desired α,β-unsaturated carboxylic acid, such as acrylic acid.

In accordance with aspects of the present invention, one such process for producing an α,β-unsaturated carboxylic acid, or a salt thereof, can comprise:

(1) contacting
  (a) a metallalactone;
  (b) a diluent; and
  (c) a solid promoter;
(2) forming an adduct of an α,β-unsaturated carboxylic acid adsorbed onto the solid promoter; and
(3) treating the adduct adsorbed onto the solid promoter to produce the α,β-unsaturated carboxylic acid, or the salt thereof.

In another aspect of this invention, a process for producing an α,β-unsaturated carboxylic acid, or a salt thereof, is provided, and in this aspect, the process can comprise:

(I) contacting
  a transition metal-ligand complex;
  (ii) an olefin;
  (iii) carbon dioxide ($CO_2$);
  (iv) a diluent; and
  (v) a solid promoter; and
(II) forming the α,β-unsaturated carboxylic acid, or the salt thereof.

Yet, in another aspect of this invention, a process for performing a metallalactone elimination reaction is provided, and in this aspect, the process can comprise:

(1) contacting
  (a) a metallalactone;
  (b) a diluent; and
  (c) a solid promoter; and
(2) forming an α,β-unsaturated carboxylic acid, or a salt thereof.

In these and other aspects, the processes disclosed herein can be used to produce, for instance, acrylic acid or a salt thereof.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects and embodiments may be directed to various feature combinations and sub-combinations described in the detailed description.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

While compositions and methods are described in terms of "comprising" various components or steps, the compositions and methods can also "consist essentially of" or "consist of" the various components or steps, unless stated otherwise.

The terms "a," "an," and "the" are intended to include plural alternatives, e.g., at least one. For instance, the disclosure of "a solid promoter," "a diluent," etc., is meant to encompass one, or mixtures or combinations of more than one, solid promoter, diluent, etc., unless otherwise specified.

The term "hydrocarbon" refers to a compound containing only carbon and hydrogen. Other identifiers may be utilized to indicate the presence of particular groups in the hydrocarbon, for instance, a halogenated hydrocarbon indicates the presence of one or more halogen atoms replacing an equivalent number of hydrogen atoms in the hydrocarbon.

As used herein, the term "α,β-unsaturated carboxylic acid" and its derivatives refer to a carboxylic acid having a carbon atom of a carbon-carbon double bond attached to the carbonyl carbon atom (the carbon atom bearing the double bonded oxygen atom). Optionally, the α,β-unsaturated carboxylic acid may contain other functional groups and/or heteroatoms.

For any particular compound or group disclosed herein, any name or structure presented is intended to encompass all conformational isomers, regioisomers, stereoisomers, and mixtures thereof that may arise from a particular set of substituents, unless otherwise specified. The name or structure also encompasses all enantiomers, diastereomers, and other optical isomers (if there are any) whether in enantiomeric or racemic forms, as well as mixtures of stereoisomers, as would be recognized by a skilled artisan, unless otherwise specified.

For example, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Various numerical ranges are disclosed herein. When Applicants disclose or claim a range of any type, Applicants' intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicants disclose, in an aspect of the invention, that one or more steps in the processes disclosed herein can be conducted at a temperature in a range from 10° C. to 75° C. This range should be interpreted as encompassing temperatures in a range from "about" 10° C. to "about" 75° C.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

The term "substituted" when used to describe a group, for example, when referring to a substituted analog of a particular group, is intended to describe the compound or group wherein any non-hydrogen moiety formally replaces hydrogen in that group or compound, and is intended to be non-limiting. A compound or group may also be referred to herein as "unsubstituted" or by equivalent terms such as "non-substituted," which refers to the original group or compound. "Substituted" is intended to be non-limiting and include inorganic substituents or organic substituents as specified and as understood by one of ordinary skill in the art.

The terms "contact product," "contacting," and the like, are used herein to describe compositions and methods wherein the components are contacted together in any order, in any manner, and for any length of time. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, "contacting" two or more components can result in a reaction product or a reaction mixture. Consequently, depending upon the circumstances, a "contact product" can be a mixture, a reaction mixture, or a reaction product.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

DETAILED DESCRIPTION OF THE INVENTION

The present invention is directed generally to methods for forming $\alpha,\beta$-unsaturated carboxylic acids, or salts thereof. An illustrative example of a suitable $\alpha,\beta$-unsaturated carboxylic acid is acrylic acid.

Solid Promoters

Generally, the solid promoter used in the processes disclosed herein can comprise (or consist essentially of, or consist of) a solid oxide, a clay or pillared clay, or combinations thereof. For instance, it is contemplated that mixtures or combinations of two or more solid promoters can be employed in certain aspects of the invention. Generally, the term solid promoter is used interchangeably herein with solid activator.

In accordance with one aspect, the solid promoter can comprise a basic promoter, for instance, a solid promoter that can act as a base. Representative and non-limiting examples of basic promoters can include alumina, titania, zirconia, magnesia, boria, calcia, zinc oxide, silica-alumina, silica-coated alumina, silica-titania, silica-zirconia, silica-magnesia, alumina-titania zinc-aluminate, alumina-boria, silica-boria, aluminum phosphate, aluminophosphate, aluminophosphate-silica, magnesium aluminate, titania-zirconia, and the like, as well as combinations thereof. In accordance with another aspect, the solid promoter can comprise a Lewis acid promoter. Representative and non-limiting examples of Lewis acid promoters can include silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, and the like, as well as combinations thereof. In accordance with yet another aspect, the solid promoter can comprise a Bronsted base promoter. Representative and non-limiting examples of Bronsted base promoters can include alumina, titania, zirconia, magnesia, boria, calcia, zinc oxide, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, and the like, as well as combinations thereof. In accordance with still another aspect, the solid promoter can comprise a Bronsted base and Lewis acid promoter. Representative and non-limiting examples of Bronsted base and Lewis acid promoters can include alumina, titania, zirconia, magnesia, boria, calcia, zinc oxide, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, and the like, as well as combinations thereof.

Consistent with aspects of this invention, the solid promoter can comprise (or consist essentially of, or consist of) a solid oxide. Generally, the solid oxide can comprise oxygen and one or more elements selected from Group 2, 3, 4, 5, 6, 7, 8, 9, 10, 11, 12, 13, 14, or 15 of the periodic table, or comprise oxygen and one or more elements selected from the lanthanide or actinide elements (See: Hawley's Condensed Chemical Dictionary, 11$^{th}$ Ed., John Wiley & Sons, 1995; Cotton, F. A., Wilkinson, G., Murillo, C. A., and Bochmann, M., Advanced Inorganic Chemistry, 6$^{th}$ Ed., Wiley-Interscience, 1999). For example and not limited thereto, the solid oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, Zr, Na, K, Cs, Ca, Ba, and Li.

Illustrative examples of solid oxides that can be used as solid promoters as described herein can include, but are not limited to, $Al_2O_3$, $B_2O_3$, $BeO$, $Bi_2O_3$, $BaO$, $MgO$, $CaO$, $CdO$, $Ce_2O_3$, $Co_3O_4$, $Cr_2O_3$, $CuO$, $Fe_2O_3$, $Ga_2O_3$, $K_2O$, $La_2O_3$, $Mn_2O_3$, $MoO_3$, $Na_2O$, $NiO$, $P_2O_5$, $Sb_2O_5$, $SiO_2$, $SnO_2$, $SrO$, $ThO_2$, $TiO_2$, $V_2O_5$, $WO_3$, $Y_2O_3$, $ZnO$, $ZrO_2$, and the like, including mixed oxides thereof, and combinations thereof. In addition to oxides, carbonates and hydroxides of the above elements also can be used, either alone or in combination.

In an aspect, the solid oxide can comprise silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, and the like, or a combination thereof; alternatively, silica; alternatively, alumina; alternatively, titania; alternatively, zirconia; alternatively, magnesia; alternatively, boria; alternatively, calcia; alternatively, zinc oxide; alternatively, silica-alumina; alternatively, silica-coated alumina; alternatively, silica-titania; alternatively, silica-zirconia; alternatively, silica-magnesia; alternatively, alumina-titania; alternatively, alumina-zirconia; alternatively, zinc-aluminate; alternatively, alumina-boria; alternatively, silica-boria; alternatively, aluminum phosphate; alternatively, aluminophosphate; alternatively, aluminophosphate-silica; alternatively, magnesium aluminate; or alternatively, titania-zirconia. In another aspect, the solid oxide can comprise magnesium aluminate, calcium aluminate, zinc aluminate, zirconium aluminate, sodium aluminate, magnesium zirconium oxide, sodium zirconium oxide, calcium zirconium oxide, lanthanum chromium oxide, barium titanium oxide, and the like, or a combination thereof; alternatively, magnesium aluminate; alternatively, calcium aluminate; alternatively, zinc aluminate; alternatively, zirconium aluminate; alternatively, sodium aluminate; alternatively, magnesium zirconium oxide; alternatively, sodium zirconium oxide; alternatively, calcium zirconium oxide; alternatively, lanthanum chromium oxide; or alternatively, barium titanium oxide. Various methods for producing suitable solid oxides and mixed solid oxides, such as co-gelling, doping or impregnating are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485, which are incorporated herein by reference in their entirety. Other suitable processes and procedures for preparing solid oxides that can be used as solid promoters are well known to those of skill in the art.

Consistent with aspects of this invention, the solid promoter can comprise (or consist essentially of, or consist of) a clay or a pillared clay. The clay or pillared clay material that can be employed as a solid promoter in the disclosed processes can encompass clay materials either in their natural state or that have been treated with various ions by wetting, ion exchange, pillaring, or other processes. In some aspects, the clay or pillared clay material can comprise clays that have been ion exchanged with large cations, including polynuclear, highly charged metal complex cations. In other aspects, the clay or pillared clay material can comprise clays that have been ion exchanged with simple salts, including, but not limited to, salts of Al(III), Fe(II), Fe(III), and Zn(II) with ligands such as halide, acetate, sulfate, nitrate, nitrite, and the like.

In another aspect, the clay or pillared clay material can comprise a pillared clay. The term "pillared clay" can be used to refer to clay materials that have been ion exchanged with large, typically polynuclear, highly charged metal complex cations. Examples of such ions include, but are not limited to, Keggin ions which can have charges such as 7+, various polyoxometallates, and other large ions. Thus, the term pillaring generally refers to a simple exchange reaction in which the exchangeable cations of a clay material can be replaced with large, highly charged ions, such as Keggin ions. These polymeric cations are then immobilized within the interlayers of the clay, and when calcined can be converted to metal oxide "pillars," effectively supporting the clay layers as column-like structures. Thus, once the clay has been dried and calcined to produce the supporting pillars between clay layers, the expanded lattice structure can be maintained and the porosity can be enhanced. The resulting pores can vary in shape and size as a function of the pillaring material and the parent clay material used, among other variables. Examples of pillaring and pillared clays are found in: T. J. Pinnavaia, *Science* 220 (4595), 365-371 (1983); J. M. Thomas, Intercalation Chemistry, (S. Whittington and A. Jacobson, eds.) Ch. 3, pp. 55-99, Academic Press, Inc., (1972); U.S. Pat. No. 4,452,910; U.S. Pat. No. 5,376,611; and U.S. Pat. No. 4,060,480; the disclosures of which are incorporated herein by reference in their entirety.

In some aspects, the clay or pillared clay can comprise montmorillonite, bentonite, nontronite, hectorite, halloysite, vermiculite, mica, fluoromica, chlorite, sepiolite, attapulgite, palygorskite, illite, saponite, allophone, smectite, kaolinite, pyrophyllite, and the like, or any combination thereof. In other aspects, the clay or pillared clay can comprise montmorillonite; alternatively, bentonite; alternatively, nontronite; alternatively, hectorite; alternatively, halloysite; alternatively, vermiculite; alternatively, mica; alternatively, fluoromica; alternatively, chlorite; alternatively, sepiolite; alternatively, attapulgite; alternatively, palygorskite; alternatively, illite; alternatively, saponite; alternatively, allophone; alternatively, smectite; alternatively, kaolinite; or alternatively, pyrophyllite.

In accordance with an aspect of this invention, the solid promoter can comprise silica, alumina, silica-alumina, aluminum phosphate, alumina-boria, silica-magnesia, silica-titania, zirconia, magnesia, magnesium aluminate, sepiolite, titania, palygorskite, montmorillonite, talc, kaolinite, halloysite, pyrophyllite, and the like, as well as combinations thereof. In accordance with another aspect, the solid promoter can comprise silica, alumina, silica-alumina, aluminum phosphate, alumina-boria, silica-magnesia, silica-titania, zirconia, magnesia, magnesium aluminate, titania, and the like, as well as combinations thereof. In accordance with yet another aspect, the solid promoter can comprise sepiolite, palygorskite, montmorillonite, talc, kaolinite, halloysite, pyrophyllite, and the like, as well as combinations thereof. In accordance with still another aspect, the solid promoter can comprise alumina, zirconia, magnesia, magnesium aluminate, sepiolite, and the like, as well as combinations thereof; alternatively, alumina; alternatively, zirconia; alternatively, magnesia; alternatively, magnesium aluminate; or alternatively, sepiolite.

The solid promoters contemplated herein can have any suitable surface area, pore volume, and particle size, as would be recognized by those of skill in the art. For instance, the solid promoter can have a pore volume in a range from 0.1 to 2.5 mL/g, or alternatively, from 0.5 to 2.5 mL/g. In a further aspect, the promoter can have a pore volume from 1 to 2.5 mL/g. Alternatively, the pore volume can be from 0.1 to 1.0 mL/g. Additionally, or alternatively, the solid promoter can have a BET surface area in a range from 10 to 750 m$^2$/g; alternatively, from 100 to 750 m$^2$/g; alternatively, from 100 to 500 m$^2$/g; or alternatively, from 30 to 200 m$^2$/g. In a further aspect, the solid promoter can have a surface area of from 100 to 400 m$^2$/g, from 200 to 450 m$^2$/g, or from 150 to 350 m$^2$/g. The average particle size of the solid promoter can vary greatly depending upon the process specifics, however, average particle sizes in the range of from 5 to 500 microns, from 10 to 250 microns, or from 25 to 200 microns, are often employed. Alternatively, 1/8 inch to 1/4 inch pellets or beads can be used.

Prior to use, these solid promoters can be calcined. The calcining step can be conducted at a variety of temperatures and time periods, and in a variety of atmospheres (an inert atmosphere, an oxidizing atmosphere, a reducing atmosphere). For instance, the calcining step can be conducted at a peak calcining temperature in a range from 150° C. to 1000° C.; alternatively, from 250° C. to 1000° C.; alternatively, from 250° C. to 950° C.; alternatively, from 250° C. to 750° C.; alternatively, from 400° C. to 700° C.; alternatively, from 300° C. to 650° C.; or alternatively, from 400° C. to 600° C. In these and other aspects, these temperature ranges also are meant to encompass circumstances where the calcining step is conducted at a series of different temperatures (e.g., an initial calcining temperature, a peak calcining temperature), instead of at a single fixed temperature, falling within the respective ranges. For instance, the calcining step can start at an initial calcining temperature, and subsequently, the temperature of the calcining step can be increased to the peak calcining temperature, for example, a peak calcining temperature in a range from 500° C. to 1000° C., or from 250° C. to 750° C.

The duration of the calcining step is not limited to any particular period of time. Hence, the calcining step can be conducted, for example, in a time period ranging from as little as 15-45 minutes to as long as 12-24 hours, or more. The appropriate calcining time can depend upon, for example, the initial/peak calcining temperature, and the atmosphere under which calcining is conducted, among other variables. Generally, however, the calcining step can be conducted in a time period that can be in a range from 45 minutes to 18 hours, such as, for example, from 45 minutes to 15 hours, from 1 hour to 12 hours, from 2 hours to 10 hours, from 3 hours to 10 hours, or from 4 hours to 10 hours.

Diluents

The processes disclosed herein typically are conducted in the presence of a diluent. Mixtures and/or combinations of diluents can be utilized in these processes. The diluent can comprise, consist essentially of, or consist of, any suitable solvent or any solvent disclosed herein, unless otherwise specified. For instance, in accordance with one aspect of this invention, the diluent can comprise a non-protic solvent. Representative and non-limiting examples of non-protic solvents can include tetrahydrofuran (THF), 2,5-Me$_2$THF, acetone, toluene, chlorobenzene, pyridine, carbon dioxide, and the like, as well as combinations thereof. In accordance with another aspect, the diluent can comprise a weakly coordinating or non-coordinating solvent. Representative and non-limiting examples of weakly coordinating or non-coordinating solvents can include toluene, chlorobenzene, paraffins, halogenated paraffins, and the like, as well as combinations thereof. In accordance with yet another aspect, the diluent can comprise a carbonyl-containing solvent, for instance, ketones, esters, amides, and the like, as well as combinations thereof. Representative and non-limiting examples of carbonyl-containing solvents can include acetone, ethyl methyl ketone, ethyl acetate, propyl acetate, butyl acetate, isobutyl isobutyrate, methyl lactate, ethyl lactate, N,N-dimethylformamide, and the like, as well as combinations thereof. In still another aspect, the diluent can comprise THF, 2,5-Me$_2$THF, methanol, acetone, toluene, chlorobenzene, pyridine, or a combination thereof; alternatively, THF; alternatively, 2,5-Me$_2$THF; alternatively, methanol; alternatively, acetone; alternatively, toluene; alternatively, chlorobenzene; or alternatively, pyridine.

In an aspect, the diluent can comprise (or consist essentially of, or consist of) an aromatic hydrocarbon solvent. Non-limiting examples of suitable aromatic hydrocarbon solvents that can be utilized singly or in any combination include benzene, toluene, xylene (inclusive of ortho-xylene, meta-xylene, para-xylene, or mixtures thereof), and ethylbenzene, or combinations thereof; alternatively, benzene; alternatively, toluene; alternatively, xylene; or alternatively, ethylbenzene.

In an aspect, the diluent can comprise (or consist essentially of, or consist of) a halogenated aromatic hydrocarbon solvent. Non-limiting examples of suitable halogenated aromatic hydrocarbon solvents that can be utilized singly or in any combination include chlorobenzene, dichlorobenzene, and combinations thereof; alternatively, chlorobenzene; or alternatively, dichlorobenzene.

In an aspect, the diluent can comprise (or consist essentially of, or consist of) an ether solvent. Non-limiting examples of suitable ether solvents that can be utilized singly or in any combination include dimethyl ether, diethyl ether, diisopropyl ether, di-n-propyl ether, di-n-butyl ether, diphenyl ether, methyl ethyl ether, methyl t-butyl ether, dihydrofuran, tetrahydrofuran (THF), 2,5-Me$_2$THF, 1,2-dimethoxyethane, 1,4-dioxane, and combinations thereof; alternatively, diethyl ether, dibutyl ether, THF, 2,5-Me$_2$THF, 1,2-dimethoxyethane, 1,4-dioxane, and combinations thereof; alternatively, THF; or alternatively, diethyl ether.

Metallalactones and Transition Metal-Ligand Complexes

Generally, the processes disclosed herein employ a metallalactone or a transition metal-ligand complex. The transition metal of the metallalactone, or of the transition metal-ligand complex, can be a Group 3 to Group 8 transition metal or, alternatively, a Group 8 to Group 11 transition metal. In one aspect, for instance, the transition metal can be Fe, Co, Ni, Cu, Ru, Rh, Pd, Ag, Ir, Pt, or Au, while in another aspect, the transition metal can be Fe, Ni, or Rh. Alternatively, the transition metal can be Fe; alternatively, the transition metal can be Co; alternatively, the transition metal can be Ni; alternatively, the transition metal can be Cu; alternatively, the transition metal can be Ru; alternatively, the transition metal can be Rh; alternatively, the transition metal can be Pd; alternatively, the transition metal can be Ag; alternatively, the transition metal can be Ir; alternatively, the transition metal can be Pt; or alternatively, the transition metal can be Au.

In particular aspects contemplated herein, the transition metal can be Ni. Hence, the metallalactone can be a nickelalactone and the transition metal-ligand complex can be a Ni-ligand complex in these aspects.

The ligand of the metallalactone, or of the transition metal-ligand complex, can be any suitable neutral electron donor group and/or Lewis base. For instance, the suitable neutral ligands can include sigma-donor solvents that contain a coordinating atom (or atoms) that can coordinate to the transition metal of the metallalactone (or of the transition metal-ligand complex). Examples of suitable coordinating atoms in the ligands can include, but are not limited to, O, N, S, and P, or combinations of these atoms. In some aspects consistent with this invention, the ligand can be a bidentate ligand.

In an aspect, the ligand used to form the metallalactone or the transition metal-ligand complex can be an ether, an organic carbonyl, a thioether, an amine, a nitrile, or a phosphine. In another aspect, the ligand used to form the metallalactone or the transition metal-ligand complex can be an acyclic ether, a cyclic ether, an acyclic organic carbonyl, a cyclic organic carbonyl, an acyclic thioether, a cyclic thioether, a nitrile, an acyclic amine, a cyclic amine, an acyclic phosphine, or a cyclic phosphine.

Suitable ethers can include, but are not limited to, dimethyl ether, diethyl ether, dipropyl ether, dibutyl ether, methyl ethyl ether, methyl propyl ether, methyl butyl ether, diphenyl ether, ditolyl ether, tetrahydrofuran, 2-methyltetrahydrofuran, 2,5-dimethyltetrahydrofuran, 2,3-dihydrofuran, 2,5-dihydrofuran, furan, benzofuran, isobenzofuran, dibenzofuran, tetrahydropyran, 3,4-dihydro-2H-pyran, 3,6-dihydro-2H-pyran, 2H-pyran, 4H-pyran, 1,3-dioxane, 1,4-dioxane, morpholine, and the like, including substituted derivatives thereof.

Suitable organic carbonyls can include ketones, aldehydes, esters, and amides, either alone or in combination, and illustrative examples can include, but are not limited to, acetone, acetophonone, benzophenone, N,N-dimethylformamide, N,N-dimethylacetamide, methyl acetate, ethyl acetate, and the like, including substituted derivatives thereof.

Suitable thioethers can include, but are not limited to, dimethyl thioether, diethyl thioether, dipropyl thioether, dibutyl thioether, methyl ethyl thioether, methyl propyl thioether, methyl butyl thioether, diphenyl thioether, ditolyl thioether, thiophene, benzothiophene, tetrahydrothiophene, thiane, and the like, including substituted derivatives thereof.

Suitable nitriles can include, but are not limited to, acetonitrile, propionitrile, butyronitrile, benzonitrile, 4-methylbenzonitrile, and the like, including substituted derivatives thereof.

Suitable amines can include, but are not limited to, methyl amine, ethyl amine, propyl amine, butyl amine, dimethyl amine, diethyl amine, dipropyl amine, dibutyl amine, trimethyl amine, triethyl amine, tripropyl amine, tributyl amine, aniline, diphenylamine, triphenylamine, tolylamine, xylylamine, ditolylamine, pyridine, quinoline, pyrrole, indole, 2-methylpyridine, 3-methylpyridine, 4-methylpyridine, 2,5-dimethylpyrrole, 2,5-diethylpyrrole, 2,5-dipropylpyrrole, 2,5-dibutylpyrrole, 2,4-dimethylpyrrole, 2,4-diethylpyrrole, 2,4-dipropylpyrrole, 2,4-dibutylpyrrole, 3,4-dimethylpyrrole, 3,4-diethylpyrrole, 3,4-dipropylpyrrole, 3,4-dibutylpyrrole, 2-methylpyrrole, 2-ethylpyrrole, 2-propylpyrrole, 2-butylpyrrole, 3-methylpyrrole, 3-ethylpyrrole, 3-propylpyrrole, 3-butylpyrrole, 3-ethyl-2,4-dimethylpyrrole, 2,3,4,5-tetramethylpyrrole, 2,3,4,5-tetraethylpyrrole, 2,2'-bipyridine, 1,8-diazabicyclo[5.4.0]undec-7-ene, di(2-pyridyl)dimethylsilane, N,N,N',N'-tetramethylethylenediamine, 1,10-phenanthroline, 2,9-dimethyl-1,10-phenanthroline, glyoxal-bis(mesityl)-1,2-diimine and the like, including substituted derivatives thereof. Suitable amines can be primary amines, secondary amines, or tertiary amines.

Suitable phosphines and other phosphorus compounds can include, but are not limited to, trimethylphosphine, triethylphosphine, tripropylphosphine, tributylphosphine, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenylphosphine, tricyclohexylphosphine, trimethyl phosphite, triethyl phosphite, tripropyl phosphite, triisopropyl phosphite, tributyl phosphite and tricyclohexyl phosphite, 2-(di-t-butylphosphino)biphenyl, 2-di-t-butylphosphino-1,1'-binaphthyl, 2-(di-t-butylphosphino)-3,6-dimethoxy-2',4',6'-tri-i-propyl-1,1'-biphenyl, 2-di-t-butylphosphino-2'-methylbiphenyl, 2-(di-t-butylphosphinomethyl)pyridine, 2-di-t-butylphosphino-2',4',6'-tri-i-propyl-1,1'-biphenyl, 2-(dicyclohexylphosphino)biphenyl, (S)-(+)-(3,5-dioxa-4-phospha-cyclohepta[2,1-a;3,4-a']dinaphthalen-4-yl)dimethylamine, 2-(diphenylphosphino)-2'-methoxy-1,1'-binaphthyl, 1,2,3,4,5-pentaphenyl-1'-(di-t-butylphosphino) ferrocene, 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino)-ethane, 1,2-bis(diisopropylphosphino)ethane, 1,2-bis(dibutyl-phosphino)ethane, 1,2-bis(di-t-butyl-phosphino) ethane, 1,2-bis(dicyclohexylphosphino)ethane, 1,3-bis(dicyclohexylphosphino)propane, 1,3-bis(diisopropylphosphino)propane, 1,3-bis(diphenylphosphino)propane, 1,3-bis(di-t-butylphosphino) propane, 1,4-bis(diisopropylphosphino)butane, 1,4-bis(diphenylphosphino)butane, 2,2'-bis[bis(3,5-dimethylphenyl)phosphino]-4,4',6,6'-tetramethoxybiphenyl, 2,6-bis(di-t-butylphosphinomethyl)pyridine, 2,2'-bis(dicyclohexylphosphino)-1,1'-biphenyl, bis(2-dicyclohexylphosphinophenyl)ether, 5,5'-bis(diphenylphosphino)-4,4'-bi-1,3-benzodioxole, 2-t-butylphosphinomethylpyridine, bis(diphenylphosphino)ferrocene, bis(diphenylphosphino) methane, bis(dicyclohexylphosphino)methane, bis(di-t-butylphosphino)methane, and the like, including substituted derivatives thereof.

In other aspects, the ligand used to form the metallalactone or the transition metal-ligand complex can be a carbene, for example, a N-heterocyclic carbene (NHC) compound. Representative and non-limiting examples of suitable N-heterocyclic carbene (NHC) materials include the following:

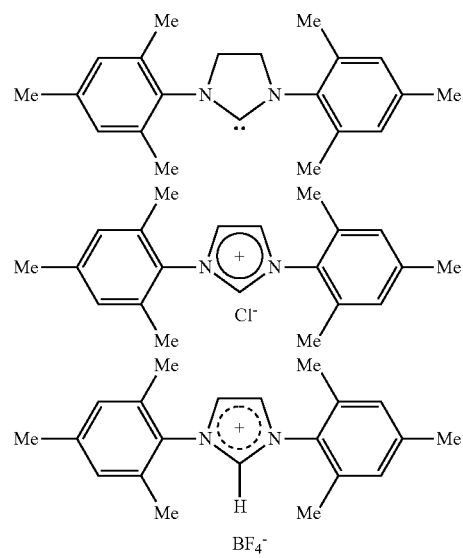

-continued

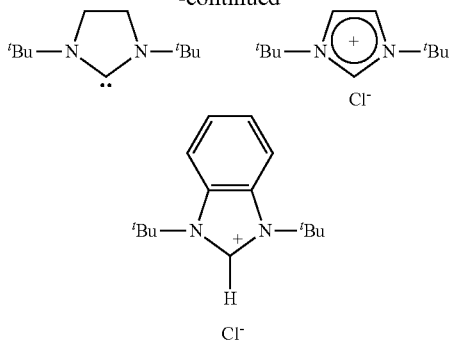

Illustrative and non-limiting examples of metallalactone complexes (representative nickelalactones) suitable for use as described herein include the following compounds (Cy=cyclohexyl, ᵗBu=tert-butyl):

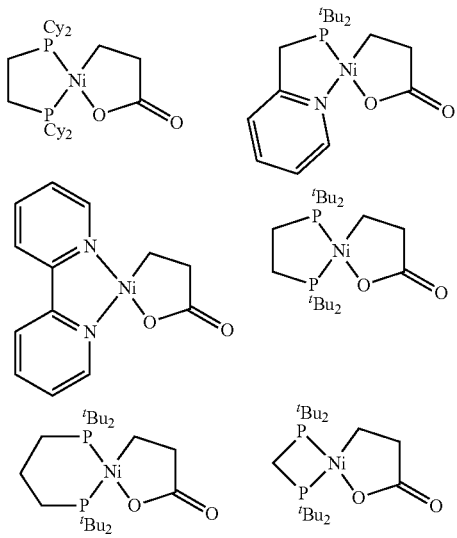

The transition metal-ligand complexes corresponding to these illustrative metallalactones are shown below:

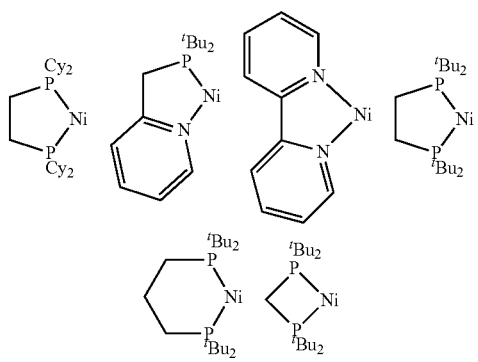

Metallalactones can be synthesized according to the following general reaction scheme (illustrated with nickel as the transition metal; Ni(COD)$_2$ is bis(1,5-cyclooctadiene)nickel (0)):

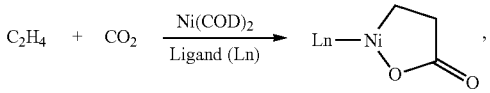

and according to suitable procedures well known to those of skill in the art.

Suitable ligands, transition metal-ligand complexes, and metallalactones are not limited solely to those ligands, transition metal-ligand complexes, and metallalactones disclosed herein. Other suitable ligands, transition metal-ligand complexes, and/or metallalactones are described, for example, in U.S. Pat. Nos. 7,250,510, 8,642,803, and 8,697,909; Journal of Organometallic Chemistry, 1983, 251, C51-053; Z. Anorg. Allg. Chem., 1989, 577, 111-114; Journal of Organometallic Chemistry, 2004, 689, 2952-2962; Organometallics, 2004, Vol. 23, 5252-5259; Chem. Commun, 2006, 2510-2512; Organometallics, 2010, Vol. 29, 2199-2202; Chem. Eur. J., 2012, 18, 14017-14025; Organometallics, 2013, 32 (7), 2152-2159; and Chem. Eur. J., 2014, Vol. 20, 11, 3205-3211; the disclosures of which are incorporated herein by reference in their entirety.

Producing α,β-Unsaturated Carboxylic Acids and Salts Thereof

Generally, the features of the processes disclosed herein (e.g., the metallalactone, the diluent, the solid promoter, the α,β-unsaturated carboxylic acid or salt thereof, the transition metal-ligand complex, the olefin, and the conditions under which the α,β-unsaturated carboxylic acid, or a salt thereof, is formed, among others) are independently described, and these features may be combined in any combination to further describe the disclosed processes.

In accordance with an aspect of the present invention, a process for performing a metallalactone elimination reaction is disclosed. This process can comprise (or consist essentially of, or consist of):

(1) contacting
(a) a metallalactone;
(b) a diluent; and
(c) a solid promoter; and
(2) forming an α,β-unsaturated carboxylic acid, or a salt thereof.

Suitable metallalactones, diluents, and solid promoters are disclosed hereinabove. In this process for performing a metallalactone elimination reaction, for instance, at least a portion of the diluent can comprise the α,β-unsaturated carboxylic acid, or the salt thereof, that is formed in step (2) of this process.

In accordance with another aspect of the present invention, a process for producing an α,β-unsaturated carboxylic acid, or a salt thereof, is disclosed. This process can comprise (or consist essentially of, or consist of):

(1) contacting
(a) a metallalactone;
(b) a diluent; and
(c) a solid promoter;
(2) forming an adduct of an α,β-unsaturated carboxylic acid adsorbed onto the solid promoter; and
(3) treating the adduct adsorbed onto the solid promoter to produce the α,β-unsaturated carboxylic acid, or the salt thereof.

In this process for producing an α,β-unsaturated carboxylic acid or a salt thereof, for instance, at least a portion of the diluent comprising a transition metal of the metallalactone can be removed after step (2), and before step (3), of this process. Suitable metallalactones, diluents, and solid promoters are disclosed hereinabove.

In some aspects, the contacting step—step (1)—of these processes can include contacting, in any order, the metallalactone, the diluent, and the solid promoter, and additional unrecited materials. In other aspects, the contacting step can consist essentially of, or consist of, the metallalactone, the diluent, and the solid promoter components. Likewise, additional materials or features can be employed in the forming step—step (2)—of these processes, and/or in the treating step—step (3)—of the process for producing the $\alpha,\beta$-unsaturated carboxylic acid, or the salt thereof. Further, it is contemplated that these processes for performing a metallalactone elimination reaction and for producing an $\alpha,\beta$-unsaturated carboxylic acid, or a salt thereof, can employ more than one metallalactone and/or more than one solid promoter. Additionally, a mixture or combination of two or more diluents can be employed.

Any suitable reactor, vessel, or container can be used to contact the metallalactone, diluent, and solid promoter, non-limiting examples of which can include a flow reactor, a continuous reactor, a fixed bed reactor, and a stirred tank reactor, including more than one reactor in series or in parallel, and including any combination of reactor types and arrangements. In particular aspects consistent with this invention, the metallalactone and the diluent contact a fixed bed of the solid promoter, for instance, in a suitable vessel, such as in a continuous fixed bed reactor. In further aspects, combinations of more than one solid promoter can be used, such as a mixed bed of a first solid promoter and a second solid promoter, or sequential beds of a first solid promoter and a second solid promoter. In these and other aspects, the feed stream can flow upward or downward through the fixed bed. For instance, the metallalactone and the diluent can contact the first solid promoter and then the second solid promoter in a downward flow orientation, and the reverse in an upward flow orientation. In a different aspect, the metallalactone and the solid promoter can be contacted by mixing or stirring in the diluent, for instance, in a suitable vessel, such as a stirred tank reactor.

Step (2) of the process for producing an $\alpha,\beta$-unsaturated carboxylic acid, or a salt thereof, recites forming an adduct of the $\alpha,\beta$-unsaturated carboxylic acid adsorbed onto the solid promoter. This adduct can contain all or a portion of the $\alpha,\beta$-unsaturated carboxylic acid, and is inclusive of salts of the $\alpha,\beta$-unsaturated carboxylic acid.

In step (3) of the process for producing an $\alpha,\beta$-unsaturated carboxylic acid or a salt thereof, the adduct adsorbed onto the solid promoter is treated to produce the $\alpha,\beta$-unsaturated carboxylic acid, or the salt thereof. Various methods can be used to liberate or desorb the $\alpha,\beta$-unsaturated carboxylic acid, or the salt thereof, from the solid promoter. In one aspect, for instance, the treating step can comprise contacting the adduct adsorbed onto the solid promoter with an acid. Representative and non-limiting examples of suitable acids can include HCl, acetic acid, and the like, as well as combinations thereof. In another aspect, the treating step can comprise contacting the adduct adsorbed onto the solid promoter with a base. Representative and non-limiting examples of suitable bases can include carbonates (e.g., $Na_2CO_3$, $Cs_2CO_3$, $MgCO_3$), hydroxides (e.g., $Mg(OH)_2$, $Na(OH)$, alkoxides (e.g., $Al(O^iPr)_3$, $Na(O^tBu)$, $Mg(OEt)_2$), and the like, as well as combinations thereof ($^iPr$=isopropyl, $^tBu$=tert-butyl, Et=ethyl). In yet another aspect, the treating step can comprise contacting the adduct adsorbed onto the solid promoter with a suitable solvent. Representative and non-limiting examples of suitable solvents can include carbonyl-containing solvents such as ketones, esters, amides, etc. (e.g., acetone, ethyl acetate, N,N-dimethylformamide, etc., as described herein above), alcohol solvents, water, and the like, as well as combinations thereof. In still another aspect, the treating step can comprise heating the adduct adsorbed onto the solid promoter to any suitable temperature. This temperature can be in a range, for example, from 50 to 1000° C., from 100 to 800° C., from 150 to 600° C., from 250 to 1000° C., from 250° C. to 550° C., or from 150° C. to 500° C. The duration of this heating step is not limited to any particular period of time, as long of the period of time is sufficient to liberate the $\alpha,\beta$-unsaturated carboxylic acid from the solid promoter. As those of skill in the art recognize, the appropriate treating step depends upon several factors, such as the particular diluent used in the process, and the particular solid promoter used in the process, amongst other considerations.

In these processes for performing a metallalactone elimination reaction and for producing an $\alpha,\beta$-unsaturated carboxylic acid (or a salt thereof), additional process steps can be conducted before, during, and/or after any of the steps described herein. As an example, these processes can further comprise a step (e.g., prior to step (1)) of contacting a transition metal-ligand complex with an olefin and carbon dioxide ($CO_2$) to form the metallalactone. Transition metal-ligand complexes are described hereinabove. Illustrative and non-limiting examples of suitable olefins can include ethylene, propylene, butene (e.g., 1-butene), pentene, hexene (e.g., 1-hexene), heptane, octene (e.g., 1-octene), and the like, as well as combinations thereof.

Yet, in accordance with another aspect of the present invention, a process for producing an $\alpha,\beta$-unsaturated carboxylic acid, or a salt thereof, is disclosed. This process can comprise (or consist essentially of, or consist of):

(I) contacting
  (i) a transition metal-ligand complex;
  (ii) an olefin;
  (iii) carbon dioxide ($CO_2$);
  (iv) a diluent; and
  (v) a solid promoter; and
(II) forming the $\alpha,\beta$-unsaturated carboxylic acid, or the salt thereof.

Suitable transition metal-ligands, olefins, diluents, and solid promoters are disclosed hereinabove. In some aspects, the contacting step—step (1)—of this process can include contacting, in any order, the transition metal-ligand, the olefin, the diluent, the solid promoter, and carbon dioxide, and additional unrecited materials. In other aspects, the contacting step can consist essentially of, or consist of, contacting, in any order, the transition metal-ligand, the olefin, the diluent, the solid promoter, and carbon dioxide. Likewise, additional materials or features can be employed in the forming step—step (2)—of this process. Further, it is contemplated that this processes for producing an $\alpha,\beta$-unsaturated carboxylic acid, or a salt thereof, can employ more than one transition metal-ligand complex and/or more than one solid promoter and/or more than one olefin. Additionally, a mixture or combination of two or more diluents can be employed. As above, any suitable reactor, vessel, or container can be used to contact the transition metal-ligand, olefin, diluent, solid promoter, and carbon dioxide, whether using a fixed bed of the solid promoter, a stirred tank for contacting (or mixing), or some other reactor configuration and process. While not wishing to be bound by the following theory, a proposed and illustrative reaction scheme for this process is provided below:

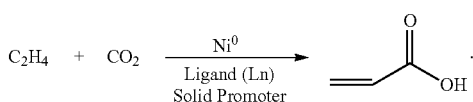

Independently, the contacting and forming steps of any of the processes disclosed herein (i.e., for performing a metallalactone elimination reaction, for producing an α,β-unsaturated carboxylic acid, or a salt thereof), can be conducted at a variety of temperatures, pressures, and time periods. For instance, the temperature at which the components in step (1) or step (I) are initially contacted can be the same as, or different from, the temperature at which the forming step is performed. As an illustrative example, in the contacting step, the components can be contacted initially at temperature T1 and, after this initial combining, the temperature can be increased to a temperature T2 for the forming step (e.g., to form the α,β-unsaturated carboxylic acid, or the salt thereof). Likewise, the pressure can be different in the contacting step and the forming step. Often, the time period in the contacting step can be referred to as the contact time, while the time period in forming step can be referred to as the reaction time. The contact time and the reaction time can be, and often are, different.

In an aspect, the contacting step and/or the forming step of the processes disclosed herein can be conducted at a temperature in a range from 0° C. to 250° C.; alternatively, from 20° C. to 200° C.; alternatively, from 0° C. to 95° C.; alternatively, from 10° C. to 75° C.; alternatively, from 10° C. to 50° C.; or alternatively, from 15° C. to 70° C. In these and other aspects, after the initial contacting, the temperature can be changed, if desired, to another temperature for the forming step. These temperature ranges also are meant to encompass circumstances where the contacting step and/or the forming step can be conducted at a series of different temperatures, instead of at a single fixed temperature, falling within the respective ranges.

In an aspect, the contacting step and/or the forming step of the processes disclosed herein can be conducted at a pressure in a range from 5 to 10,000 psig, such as, for example, from 5 to 2500 psig. In some aspects, the pressure can be in a range from 5 to 500 psig; alternatively, from 25 to 3000 psig; alternatively, from 45 to 1000 psig; or alternatively, from 50 to 250 psig.

The contacting step of the processes is not limited to any particular duration of time. That is, the respective components can be initially contacted rapidly, or over a longer period of time, before commencing the forming step. Hence, the contacting step can be conducted, for example, in a time period ranging from as little as 1-30 seconds to as long as 1-12 hours, or more. In non-continuous or batch operations, the appropriate reaction time for the forming step can depend upon, for example, the reaction temperature, the reaction pressure, and the ratios of the respective components in the contacting step, among other variables. Generally, however, the forming step can occur over a time period that can be in a range from 1 minute to 96 hours, such as, for example, from 2 minutes to 96 hours, from 5 minutes to 72 hours, from 10 minutes to 72 hours, or from 15 minutes to 48 hours.

If the process employed is a continuous process, then the metallalactone/solid promoter catalyst contact/reaction time (or the transition metal-ligand/solid promoter catalyst contact/reaction time) can be expressed in terms of weight hourly space velocity (WHSV)—the ratio of the weight of the metallalactone (or transition metal-ligand complex) which comes in contact with a given weight of solid promoter per unit time. While not limited thereto, the WHSV employed, based on the amount of the solid promoter, can be in a range from 0.05 to 100, from 0.05 to 50, from 0.075 to 50, from 0.1 to 25, from 0.5 to 10, from 1 to 25, or from 1 to 5.

In the processes disclosed herein, the molar yield of the α,β-unsaturated carboxylic acid, or the salt thereof), based on the metallalactone (or the transition metal-ligand complex) is at least 2%, and more often can be at least 5%, at least 10%, or at least 15%. In particular aspects of this invention, the molar yield can be at least 18%, at least 20%, at least 25%, at least 35%, at least 50%, at least 60%, at least 75%, or at least 85%, and often can range up to 90%, or 95%, or 100%.

The specific α,β-unsaturated carboxylic acid (or salt thereof) that can be formed or produced using the processes of this invention is not particularly limited. Illustrative and non-limiting examples of the α,β-unsaturated carboxylic acid can include acrylic acid, methacrylic acid, 2-ethylacrylic acid, and the like, as well as combinations thereof. Illustrative and non-limiting examples of the salt of the α,β-unsaturated carboxylic acid can include sodium acrylate, magnesium acrylate, sodium methacrylate, and the like, as well as combinations thereof.

Once formed, the α,β-unsaturated carboxylic acid (or salt thereof) can be purified and/or isolated and/or separated using suitable techniques which can include, but are not limited to, evaporation, distillation, chromatography, crystallization, extraction, washing, decanting, filtering, drying, and the like, including combinations of more than one of these techniques. In an aspect, the process can for performing a metallalactone elimination reaction (or the process for producing an α,β-unsaturated carboxylic acid, or a salt thereof) can further comprise a step of separating or isolating the α,β-unsaturated carboxylic acid (or salt thereof) from other components, e.g., the diluent, the solid promoter, etc.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

The following nickelalactone complexes, which can be derived from $CO_2$—ethylene coupling, were used to evaluate various homogeneous and heterogeneous (solid) promoters in the examples that follow.

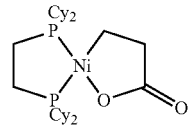

-continued

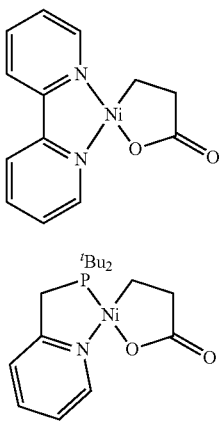

The general nickelalactone elimination reaction was performed as follows. A flask was charged with 10 mg of nickelalactone (A, B, or C), promoter, and approximately 10 mL of diluent. The reaction mixture was heated with vigorous stirring on an oil bath under conditions described in the examples below. The reaction mixture was allowed to cool to ambient temperature, then acidified. The yield of acrylic acid was determined by $^1$H NMR in $D_6$-acetone versus an internal standard sorbic acid stock solution.

Examples 1-8

Evaluation of Homogeneous Activators/Promoters

Acrylate Elimination

For Examples 1-8, 5 equivalents of the activator/promoter (per Ni) were incubated with the nickelalactone (A, B, or C) at 50° C. for 3 hours, followed by eventual acid hydrolysis and extraction to quantify the amount of acrylic acid by $^1$H NMR against an internal standard, as reflected in the following reaction scheme:

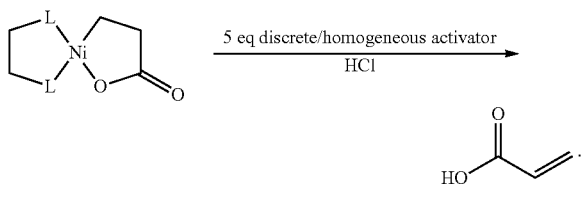

The results of the evaluation of the homogeneous activators/promoters are summarized in Table I. The diluents employed in Example 1 and Examples 2-7 were 5:1 tetrahydrofuran/acetone and tetrahydrofuran, respectively. Example 8 was investigated in tetrahydrofuran, methanol, and acetone. The homogeneous promoter of Example 5 was a solution of methylaluminoxane in toluene, while the homogeneous promoter of Example 6 was a mixture of Mg("Bu)$_2$ and methanol, which results in an alkoxide. As shown in Table I, the homogeneous activators/promoters of Examples 1-8 failed to yield any acrylic acid with any of the nickelalactones investigated.

TABLE I

Molar Yields of Examples 1-8.

| Example | Promoter | A | B | C |
|---|---|---|---|---|
| 1 | Na$_2$(CO$_3$) | 0 | 0 | 0 |
| 2 | Al(CH$_2$CH$_3$)$_3$ | 0 | 0 | 0 |
| 3 | Al(OCH$_2$CH$_3$)$_3$ | 0 | 0 | 0 |
| 4 | Ti(O$^i$Pr)$_4$ | 0 | — | — |
| 5 | (Al(CH$_3$)O)$_n$ | 0 | — | — |
| 6 | Mg("Bu)$_2$ + MeOH | 0 | — | — |
| 7 | Ca(OMe)$_2$ | 0 | — | — |
| 8 | Mg(OH)$_2$ | 0 | — | — |

Notes:
Me = methyl; $^i$Pr = isopropyl; "Bu = n-butyl.

Examples 9-12

Evaluation of Solid/Heterogeneous Activators/Promoters

Acrylate Elimination

Examples 9-12 were performed in a manner similar to that of Examples 2-7, as reflected in the following reaction scheme (25 equivalents per Ni were based on site concentration (mmol/g) of the solid activator/promoter; HCl was used to liberate the acrylic acid for analysis):

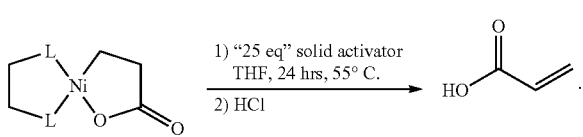

The results of the evaluation of the solid/heterogeneous activators/promoters (calcined at 400° C.) are summarized in Table II. Unexpectedly, in contrast with the homogeneous Al and Mg promoters of Examples 2-3, 5-6, and 8, the solid promoters of Examples 9-12 produced a measurable amount of acrylic acid. More surprisingly, Example 11A and 11C (zirconia) and Example 12A and 12C (magnesia) provided significant molar yields of acrylic acid (from 20% to 90%).

TABLE II

Molar Yields of Examples 9-12.

| Example | Promoter | Site conc. (mmol/g) | A | B | C |
|---|---|---|---|---|---|
| 9 | alumina | 5.4 | 0 | 0 | 11 |
| 10 | silica-magnesia | 5.3 | Trace | 0 | 0 |
| 11 | zirconia | 1.3 | 23 | 0 | 23 |
| 12 | magnesia | 1.1 | 88 | 6 | 58 |

Examples 13-24

Evaluation of Solid/Heterogeneous Activators/Promoters

Acrylate Elimination

Examples 13-24 were performed in a manner similar to that of Examples 9-12, with only nickelatactone A, as reflected in the following reaction scheme (25 equivalents per Ni were based on site concentration (mmol/g) of the solid activator/promoter; HCl was used to liberate the acrylic acid for analysis):

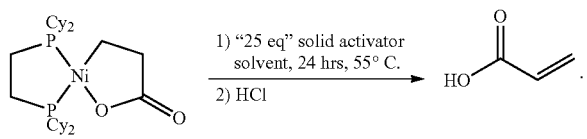

The results of the evaluation of the solid/heterogeneous activators/promoters (calcined at 400° C.) in different diluents/solvents are summarized in Table III. Unexpectedly, alumina, zirconia, magnesia, magnesium aluminate, and sepiolite produced significant amounts of acrylic acid using different diluents, with generally from 5% to 90% molar yield.

Magnesium aluminate was further tested under different calcining conditions. At 400° C. in THF diluent, the yield was 37%. Calcining at 250° C. reduced the yield to 6%, while calcining at 550° C. increased the yield to 47%.

TABLE III

Molar Yields of Examples 13-24.

| Example | Promoter | Site conc. (mmol/g) | THF | 2,5-Me$_2$THF | Methanol | Acetone | Toluene | Chlorobenzene |
|---|---|---|---|---|---|---|---|---|
| 13 | silica | 1.0 | 0 | — | — | 0 | 0 | 0 |
| 14 | alumina | 5.4 | 10 | — | 0 | 12 | 12 | 38 |
| 15 | silica-alumina | 5.0 | 4 | — | 0 | 0 | 0 | 0 |
| 16 | aluminum phosphate | 4.0 | 0 | — | — | 0 | 0 | 0 |
| 17 | alumina-boria | 5.4 | trace | — | — | 0 | 0 | trace |
| 18 | silica-magnesia | 5.3 | trace | — | 0 | trace | 0 | 0 |
| 19 | silica-titania | 5.4 | 6 | — | — | 0 | 0 | 0 |
| 20 | zirconia | 1.3 | 23 | — | 0 | 5 | 0 | — |
| 21 | magnesia | 1.1 | 88 | 27 | 0 | 33 | 18 | 45 |
| 22 | magnesium aluminate | 1.1 | 37 | 30 | — | — | 43 | 41 |
| 23 | sepiolite | 2.2 | 17 | — | — | 0 | trace | 12 |
| 24 | titania | 1.4 | 0 | — | — | 0 | 0 | 0 |

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments typically are described as "comprising" but, alternatively, can "consist essentially of" or "consist of" unless specifically stated otherwise):

Embodiment 1

A process for performing a metallalactone elimination reaction, the process comprising:
(1) contacting
(a) a metallalactone;
(b) a diluent; and
(c) a solid promoter; and
(2) forming an α,β-unsaturated carboxylic acid, or a salt thereof.

Embodiment 2

The process defined in embodiment 1, wherein at least a portion of the diluent comprises the α,β-unsaturated carboxylic acid, or the salt thereof, formed in step (2).

Embodiment 3

A process for producing an α,β-unsaturated carboxylic acid, or a salt thereof, the process comprising:
(1) contacting
(a) a metallalactone;
(b) a diluent; and
(c) a solid promoter;
(2) forming an adduct of an α,β-unsaturated carboxylic acid adsorbed onto the solid promoter; and
(3) treating the adduct adsorbed onto the solid promoter to produce the α,β-unsaturated carboxylic acid, or the salt thereof.

Embodiment 4

The process defined in embodiment 3, wherein at least a portion of the diluent comprising a transition metal of the metallalactone is removed after step (2).

Embodiment 5

The process defined in any one of embodiments 1-4, wherein in step (1), the metallalactone and the diluent contact a fixed bed of the solid promoter.

Embodiment 6

The process defined in any one of embodiments 1-4, wherein in step (1), the metallalactone and the solid promoter are contacted by mixing/stirring in the diluent.

Embodiment 7

The process defined in any one of embodiments 3-6, wherein the treating step comprises contacting the adduct adsorbed onto the solid promoter with any suitable acid, or any acid disclosed herein, e.g., HCl, acetic acid, etc.

Embodiment 8

The process defined in any one of embodiments 3-6, wherein the treating step comprises contacting the adduct adsorbed onto the solid promoter with any suitable base, or any base disclosed herein, e.g., carbonates (e.g., Na$_2$CO$_3$, $Cs_2CO_3$, $MgCO_3$), hydroxides (e.g., $Mg(OH)_2$, NaOH), alkoxides (e.g., $Al(O^iPr)_3$, $Na(O^tBu)$, $Mg(OEt)_2$), etc.

Embodiment 9

The process defined in any one of embodiments 3-6, wherein the treating step comprises contacting the adduct adsorbed onto the solid promoter with any suitable solvent, or any solvent disclosed herein, e.g., carbonyl-containing solvents such as ketones, esters, amides, etc. (e.g., acetone, ethyl acetate, N,N-dimethylformamide), alcohol solvents, water, etc.

Embodiment 10

The process defined in any one of embodiments 3-6, wherein the treating step comprises heating the adduct adsorbed onto the solid promoter to any suitable temperature, or a temperature in any range disclosed herein, e.g., from 50 to 1000° C., from 100 to 800° C., from 150 to 600° C., from 250 to 550° C., etc.

Embodiment 11

The process defined in any one of the preceding embodiments, further comprising a step of contacting a transition metal-ligand complex with an olefin and carbon dioxide ($CO_2$) to form the metallalactone.

Embodiment 12

A process for producing an $\alpha,\beta$-unsaturated carboxylic acid, or a salt thereof, the process comprising:
(I) contacting
(i) a transition metal-ligand complex;
(ii) an olefin;
(iii) carbon dioxide ($CO_2$);
(iv) a diluent; and
(v) a solid promoter; and
(II) forming the $\alpha,\beta$-unsaturated carboxylic acid, or the salt thereof.

Embodiment 13

The process defined in embodiment 11 or 12, wherein the olefin comprises any suitable olefin or any olefin disclosed herein, e.g. ethylene, propylene, 1-butene, etc.

Embodiment 14

The process defined in any one of embodiments 1-13, wherein the $\alpha,\beta$-unsaturated carboxylic acid, or a salt thereof, comprises any suitable $\alpha,\beta$-unsaturated carboxylic acid, or any $\alpha,\beta$-unsaturated carboxylic acid disclosed herein, or a salt thereof, e.g., acrylic acid, methacrylic acid, 2-ethylacrylic acid, sodium acrylate, magnesium acrylate, sodium methacrylate, etc.

Embodiment 15

The process defined in any one of embodiments 1-14, wherein the molar yield of the $\alpha,\beta$-unsaturated carboxylic acid, or the salt thereof, based on the metallalactone (or the transition metal-ligand complex) is in any range disclosed herein, e.g., at least 5%, at least 10%, at least 20%, from 5% to 95%, from 5% to 90%, from 10% to 95%, from 10% to 90%, from 15% to 95%, etc.

Embodiment 16

The process defined in any one of embodiments 1-15, wherein the process further comprises a step of isolating the $\alpha,\beta$-unsaturated carboxylic acid, or the salt thereof, e.g., using any suitable separation/purification procedure or any separation/purification procedure disclosed herein, e.g., evaporation, distillation, chromatography, etc.

Embodiment 17

The process defined in any one of embodiments 1-16, wherein the contacting step and/or the forming step is/are conducted at any suitable pressure or at any pressure disclosed herein, e.g., from 5 psig to 10,000 psig, from 45 psig to 1000 psig, etc.

Embodiment 18

The process defined in any one of embodiments 1-17, wherein the contacting step and/or the forming step is/are conducted at any suitable temperature or at any temperature disclosed herein, e.g., from 0° C. to 250° C., from 0° C. to 95° C., from 15° C. to 70° C., etc.

Embodiment 19

The process defined in any one of embodiments 1-18, wherein the contacting step is conducted at any suitable weight hourly space velocity (WHSV) or any WHSV disclosed herein, e.g., from 0.05 to 50, from 1 to 25, from 1 to 5, etc., based on the amount of the solid promoter.

Embodiment 20

The process defined in any one of embodiments 1-19, wherein the solid promoter comprises any suitable basic promoter, or any basic promoter disclosed herein.

Embodiment 21

The process defined in any one of embodiments 1-19, wherein the solid promoter comprises any suitable Lewis acid promoter.

Embodiment 22

The process defined in any one of embodiments 1-19, wherein the solid promoter comprises any suitable Bronsted base promoter, or any Bronsted base promoter disclosed herein.

Embodiment 23

The process defined in any one of embodiments 1-19, wherein the solid promoter comprises any suitable Bronsted base and Lewis acid promoter, or any Bronsted base and Lewis acid promoter disclosed herein.

Embodiment 24

The process defined in any one of embodiments 1-19, wherein the solid promoter comprises any suitable solid oxide, or any solid oxide disclosed herein.

Embodiment 25

The process defined in embodiment 24, wherein the solid oxide comprises $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, $Na_2O$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, $K_2O$, CaO, $La_2O_3$, or $Ce_2O_3$, including mixed oxides thereof, and combinations thereof.

Embodiment 26

The process defined in embodiment 24, wherein the solid oxide comprises silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, or a combination thereof.

Embodiment 27

The process defined in embodiment 24, wherein the solid oxide comprises magnesium aluminate, calcium aluminate, zinc aluminate, zirconium aluminate, sodium aluminate, magnesium zirconium oxide, sodium zirconium oxide, calcium zirconium oxide, lanthanum chromium oxide, barium titanium oxide, or a combination thereof.

Embodiment 28

The process defined in any one of embodiments 1-19, wherein the solid promoter comprises any suitable clay or pillared clay, or any clay or pillared clay disclosed herein.

Embodiment 29

The process defined in embodiment 28, wherein the clay or pillared clay comprises montmorillonite, bentonite, nontronite, hectorite, halloysite, vermiculite, mica, fluoromica, chlorite, sepiolite, attapulgite, palygorskite, illite, saponite, allophone, smectite, kaolinite, pyrophyllite, or a combination thereof.

Embodiment 30

The process defined in any one of embodiments 1-19, wherein the solid promoter comprises silica, alumina, silica-alumina, aluminum phosphate, alumina-boria, silica-magnesia, silica-titania, zirconia, magnesia, magnesium aluminate, sepiolite, titania, palygorskite, montmorillonite, talc, kaolinite, halloysite, pyrophyllite, or a combination thereof.

Embodiment 31

The process defined in any one of embodiments 1-19, wherein the solid promoter comprises alumina, zirconia, magnesia, magnesium aluminate, sepiolite, or a combination thereof.

Embodiment 32

The process defined in any one of embodiments 1-31, wherein the solid promoter has any suitable surface area, or a surface area in any range disclosed herein, e.g., from 10 to 750 $m^2/g$, from 20 to 500 $m^2/g$, from 30 to 350 $m^2/g$, etc.

Embodiment 33

The process defined in any one of embodiments 1-32, wherein the solid promoter has any suitable pore volume, or a pore volume in any range disclosed herein, e.g., from 0.1 to 2.5 mL/g, from 0.1 to 1.5 mL/g, from 0.2 to 1.0 mL/g, etc.

Embodiment 34

The process defined in any one of embodiments 1-33, wherein prior to step (1) or step (I), the solid promoter is calcined at any suitable temperature, or at a temperature in any range disclosed herein, e.g. from 150° C. to 1000° C., from 200° C. to 750° C., from 300° C. to 600° C., etc.

Embodiment 35

The process defined in any one of embodiments 1-34, wherein the diluent comprises any suitable non-protic solvent, or any non-protic solvent disclosed herein.

Embodiment 36

The process defined in any one of embodiments 1-34, wherein the diluent comprises any suitable weakly coordinating or non-coordinating solvent, or any weakly coordinating or non-coordinating solvent disclosed herein.

Embodiment 37

The process defined in any one of embodiments 1-34, wherein the diluent comprises any suitable carbonyl-containing solvent, or any carbonyl-containing solvent disclosed herein, e.g., ketones, esters, amides, etc. (e.g., acetone, ethyl acetate, N,N-dimethylformamide, etc.).

Embodiment 38

The process defined in any one of embodiments 1-34, wherein the diluent comprises any suitable ether solvent, or any ether solvent disclosed herein, e.g., THF, dimethyl ether, diethyl ether, dibutyl ether, etc.

Embodiment 39

The process defined in any one of embodiments 1-34, wherein the diluent comprises any suitable aromatic hydrocarbon solvent, or any aromatic hydrocarbon solvent disclosed herein, e.g., benzene, xylene, toluene, etc.

Embodiment 40

The process defined in any one of embodiments 1-34, wherein the diluent comprises any suitable halogenated aromatic hydrocarbon solvent, or any halogenated aromatic hydrocarbon solvent disclosed herein, chlorobenzene, dichlorobenzene, etc.

Embodiment 41

The process defined in any one of embodiments 1-34, wherein the diluent comprises THF, 2,5-$Me_2$THF, methanol, acetone, toluene, chlorobenzene, pyridine, or a combination thereof.

Embodiment 42

The process defined in any one of embodiments 1-41, wherein the transition metal of the metallalactone (or of the transition metal-ligand complex) is a Group 8-11 transition metal.

Embodiment 43

The process defined in any one of embodiments 1-41, wherein the transition metal of the metallalactone (or of the transition metal-ligand complex) is Fe, Co, Ni, Cu, Ru, Rh, Pd, Ag, Ir, Pt, or Au.

Embodiment 44

The process defined in any one of embodiments 1-41, wherein the transition metal of the metallalactone (or of the transition metal-ligand complex) is Ni, Fe, or Rh.

Embodiment 45

The process defined in any one of embodiments 1-41, wherein the metallalactone is a nickelalactone, e.g., any suitable nickelalactone or any nickelalactone disclosed herein.

Embodiment 46

The process defined in any one of embodiments 1-45, wherein the ligand of the metallalactone (or of the transition metal-ligand complex) is any suitable neutral electron donor group and/or Lewis base, or any neutral electron donor group and/or Lewis base disclosed herein.

Embodiment 47

The process defined in any one of embodiments 1-45, wherein the ligand of the metallalactone (or of the transition metal-ligand complex) is a bidentate ligand.

Embodiment 48

The process defined in any one of embodiments 1-47, wherein the ligand of the metallalactone (or of the transition metal-ligand complex) comprises at least one of a nitrogen, phosphorus, sulfur, or oxygen heteroatom.

Embodiment 49

The process defined in any one of embodiments 1-47, wherein the ligand of the metallalactone (or of the transition metal-ligand complex) is any suitable carbene group or any carbene group disclosed herein.

Embodiment 50

The process defined in any one of embodiments 1-47, wherein the metallalactone, ligand, or transition metal-ligand complex is any suitable metallalactone, ligand, or transition metal-ligand complex, or is any metallalactone, ligand, or transition metal-ligand complex disclosed herein.

We claim:

1. A process for performing a metallalactone elimination reaction, the process comprising:
   (1) forming a reaction mixture consisting essentially of
   (a) a metallalactone;
   (b) a diluent; and
   (c) a solid promoter selected from the group consisting of alumina, zirconia, magnesia, magnesium aluminate, and sepiolite, or a combination thereof; and
   (2) forming an $\alpha,\beta$-unsaturated carboxylic acid, or a salt thereof;
   wherein the molar yield of the $\alpha,\beta$-unsaturated carboxylic acid, or the salt thereof, based on the metallalactone, is at least 5%.

2. The process of claim 1, wherein:
   the $\alpha,\beta$-unsaturated carboxylic acid comprises acrylic acid.

3. The process of claim 1, wherein in step (1), the metallalactone and the diluent contact a fixed bed of the solid promoter.

4. The process of claim 1, wherein the metallalactone is a nickelalactone.

5. A process for producing an $\alpha,\beta$-unsaturated carboxylic acid, or a salt thereof, the process comprising:
   (1) contacting
   (a) a metallalactone;
   (b) a diluent; and
   (c) a solid oxide;
   (2) forming an adduct of an $\alpha,\beta$-unsaturated carboxylic acid adsorbed onto the solid oxide; and
   (3) contacting the adduct adsorbed onto the solid oxide with an acid to produce the $\alpha,\beta$-unsaturated carboxylic acid, or the salt thereof.

6. The process of claim 5, wherein:
   the $\alpha,\beta$-unsaturated carboxylic acid, or the salt thereof, comprises acrylic acid, methacrylic acid, 2-ethylacrylic acid, sodium acrylate, magnesium acrylate, sodium methacrylate, or a combination thereof; and
   the molar yield of the $\alpha,\beta$-unsaturated carboxylic acid, or the salt thereof, based on the metallalactone, is at least 5%.

7. The process of claim 5, wherein:
   the metallalactone is a nickelalactone;
   the solid oxide is a Bronsted base and a Lewis acid; and
   the $\alpha,\beta$-unsaturated carboxylic acid comprises acrylic acid.

8. The process of claim 5, wherein:
   the solid oxide comprises silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, or a combination thereof; and
   the molar yield of the $\alpha,\beta$-unsaturated carboxylic acid, or the salt thereof, based on the metallalactone, is at least 5%.

9. The process of claim 5, wherein:
   the solid oxide comprises magnesium aluminate, calcium aluminate, zinc aluminate, zirconium aluminate, sodium aluminate, magnesium zirconium oxide, sodium zirconium oxide, calcium zirconium oxide, lanthanum chromium oxide, barium titanium oxide, or a combination thereof; and
   the molar yield of the $\alpha,\beta$-unsaturated carboxylic acid, or the salt thereof, based on the metallalactone, is at least 5%.

10. The process of claim 5, wherein:
    the molar yield of the $\alpha,\beta$-unsaturated carboxylic acid, or the salt thereof, based on the metallalactone, is at least 5%;
    the metallalactone is a nickelalactone; and
    the $\alpha,\beta$-unsaturated carboxylic acid comprises acrylic acid.

11. The process of claim 5, wherein:
the solid oxide comprises alumina, zirconia, magnesia, magnesium aluminate, sepiolite, or a combination thereof; and
the molar yield of the α,β-unsaturated carboxylic acid, or the salt thereof, based on the metallalactone, is at least 10%.

12. The process of claim 5, wherein the metallalactone comprises:

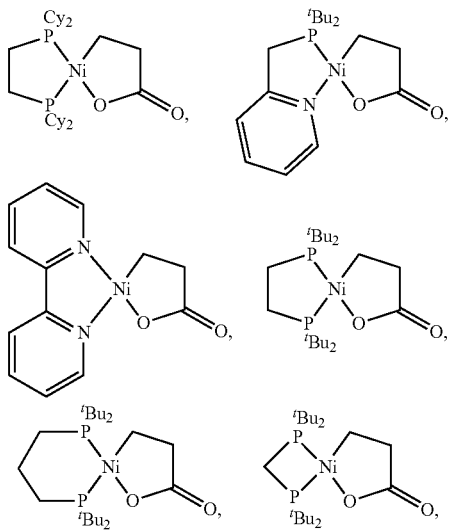

or a combination thereof, wherein Cy is cyclohexyl and $^t$Bu is tert-butyl.

13. A process for producing an α,β-unsaturated carboxylic acid, or a salt thereof, the process comprising:
(I) forming a reaction mixture consisting essentially of
(i) a transition metal-ligand complex;
(ii) an olefin;
(iii) carbon dioxide (CO2);
(iv) a diluent; and
(v) a solid promoter selected from the group consisting of magnesium aluminate, calcium aluminate, zinc aluminate, zirconium aluminate, sodium aluminate, magnesium zirconium oxide, sodium zirconium oxide, calcium zirconium oxide, lanthanum chromium oxide, barium titanium oxide, alumina, zirconia, magnesia, magnesium aluminate, and sepiolite, or a combination thereof; and
(II) forming the α,β-unsaturated carboxylic acid, or the salt thereof;
wherein the molar yield of the α,β-unsaturated carboxylic acid, or the salt thereof, based on the transition metal-ligand complex, is at least 5%.

14. The process of claim 13, wherein:
the olefin comprises ethylene; and
the α,β-unsaturated carboxylic acid comprises acrylic acid.

15. The process of claim 13, wherein the transition metal of the transition metal-ligand complex is a Group 8-11 transition metal, and the ligand of the transition metal-ligand complex is a neutral electron donor group or Lewis base.

16. The process of claim 13, wherein
the solid promoter is a Lewis acid.

17. The process of claim 13, wherein the solid promoter is magnesium aluminate, calcium aluminate, zinc aluminate, zirconium aluminate, sodium aluminate, magnesium zirconium oxide, sodium zirconium oxide, calcium zirconium oxide, lanthanum chromium oxide, barium titanium oxide, or a combination thereof.

18. The process of claim 13, wherein the solid promoter is alumina, zirconia, magnesia, magnesium aluminate, sepiolite, or a combination thereof.

19. The process of claim 13, wherein in step (I), the transition metal-ligand complex, the olefin, the carbon dioxide, and the diluent contact a fixed bed of the solid promoter.

* * * * *